(12) United States Patent
Dodge et al.

(10) Patent No.: US 6,630,508 B1
(45) Date of Patent: Oct. 7, 2003

(54) SUBSTITUTED BENZOPYRANS AS SELECTIVE ESTROGEN RECEPTOR β AGONISTS

(75) Inventors: Jeffrey Alan Dodge, Indianapolis, IN (US); Venkatesh Krishnan, Fishers, IN (US); Charles Willis Lugar, III, McCordsville, IN (US); Blake Lee Neubauer, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/349,521

(22) Filed: Jan. 22, 2003

Related U.S. Application Data

(60) Provisional application No. 60/355,891, filed on Feb. 11, 2002.

(51) Int. Cl.[7] ..................... A61K 31/352; C07D 311/78
(52) U.S. Cl. ........................................ 514/454; 549/385
(58) Field of Search ........................... 514/454; 549/385

(56) References Cited

FOREIGN PATENT DOCUMENTS

| WO | WO99/02512 | 1/1999 |
|---|---|---|
| WO | WO01/64665 A1 | 2/2001 |

OTHER PUBLICATIONS

Kedar Shanker Shrestha, et al.: *"Facile Synthesis of the Fused 6,6,5 Ring System Containing Chroman Ring From 2–(1–Hydroxy–5–alkenyl)pheno Derivitatives via Intramolecular Inverse–Electron–Demand Diels–Alder Reaction"*; Bull. Chem. Soc. Japan, vol. 72, No. 1, 1999, pp. 73–83.

K. W. Anderson, et al.: *"Synthesis of 6,9–bisnormethyl–8–methoxy–12, 13–epoxy–6,8,10–trichothecatrine"*; Journal of Organic Chemistry, vol. 42, No. 6, 1977, pp. 1045–1050.

B. A. M. Oude–Alink, et al.: *"Photolysis of 2–keto–2,3–dihydrobenzofurans, o–hydroxyphenyl)–1,5–hexadienes"*; Journal of Organic Chemistry, vol. 38, No. 11, 1973, pp. 1993–2001.

*Primary Examiner*—Charanjit S. Aulakh
(74) *Attorney, Agent, or Firm*—Michael J. Sayles

(57) ABSTRACT

The present invention relates to substituted benzopyran derivatives, stereoisomers, and pharmaceutical acceptable salts thereof and processes for the preparation of the same. The compounds of the present invention are useful as Estrogen Receptor β agonists. Such agonists are useful for treating Estrogen Receptor β mediated diseases such as prostate cancer.

13 Claims, No Drawings

SUBSTITUTED BENZOPYRANS AS SELECTIVE ESTROGEN RECEPTOR β AGONISTS

This application claims benefit of 60/355,891 filed Feb. 11, 2002.

BACKGROUND OF THE INVENTION

The present invention relates to novel cycloalkyl-benzopyrans and derivatives thereof, compositions containing those compounds, their use as selective estrogen receptor-beta agonists, and their use in the treatment of estrogen receptor-beta mediated diseases such as prostate cancer, benign prostatic hyperplasia, testicular cancer, ovarian cancer, lung cancer, cardiovascular diseases, neurodegenerative disorders, urinary incontinence, central nervous system (CNS) conditions, gastrointestinal (GI) tract conditions, and osteoporosis.

Estrogens play important roles in the development and homeostasis of the reproductive, central nervous, skeletal, and cardiovascular systems of both males and females. The estrogen receptor (ER) is currently the only member of the steroid subfamily of nuclear receptors that has different subtypes. Recently, a new ER isoform, ER-beta (also known as ER-beta1) was cloned from a rat prostatic cDNA library and is present in murine and human prostates. Consequently, the previous ER is now designated as ER-alpha. ER-alpha and ER-beta share high amino acid homology, have similar 17-β Estradiol (E2) binding affinities, and can hetero- or homodimerize to form a signaling complex; Kuiper G G, et al., Endocrinol. 138: 863–70 (1997); Kuiper G G et al., Proc. Natl. Acad. Sci. USA 93: 5925–30 (1996). Although E2 activates both ER-alpha and ER-beta, ER-alpha stimulates transcription and cellular proliferation, while ER-beta suppresses ER-alpha activation. Interestingly, 3-beta, 17-beta-androstanediol and 5-alpha-androstane have been proposed to be endogenous ligands for ER-beta; Weihua Z. et al. PNAS 98:6330–5 (2001). 3-Beta, 17-beta-androstanediol is a major metabolite of dihydrotestosterone (DHT), the 5-alpha-reduced active intracellular androgen in male accessory sex organs. ER-beta activation also stimulates increased glutathione S-transferase and quinone reductase expression. These two enzymes have been shown to possess chemoprotective detoxification properties; Chang W Y et al., Prostate 40: 115–24 (1999); Montano M M et al., J. Biol. Chem. 273: 25443–9 (1998).

With the recent identification of ER-beta, and the recognition that ER-alpha and ER-beta have different biological roles, ER-selective modulators would similarly possess significant clinical utility. Since ER-beta is strongly expressed in a number of tissues including prostate, bladder, ovary, testis, lung, small intestine, vascular endothelium, and various parts of the brain, compounds that selectively modulate ER-beta would be of clinical importance in the treatment of a variety of disease conditions, such as prostate cancer, testicular cancer, ovarian cancer, lung cancer, cardiovascular diseases, neurodegenerative disorders, urinary incontinence, CNS disorders, GI tract conditions, and osteoporosis. Such compounds would have minimal effect on tissues that contain ER-alpha, and thus exhibit different side-effect profiles. Thus, ER-beta agonists will display different therapeutic profiles compared to ER-alpha antagonists or agonists, and would be preferentially beneficial in tissues relying on ER-beta signaling.

The prostate gland produces components that are found in the semen and blood. Some of these are regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasia (BPH), which is one common prostate disease. BPH is a progressive condition that is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an inescapable phenomenon for the aging male population. BPH is observed in approximately 70% of males over the age of 70. Drug treatment for BPH currently employs alpha andrenergic antagonists for symptomatic relief or steroid 5-alpha reductase inhibitors to reduce hyperplastic tissue bulk. These approaches are of limited therapeutic benefit.

Mortality due to prostatic cancer when the strategem of watchful waiting is adopted is generally low (9%–15%) in men who have localized tumors. However, these rates pertain to patients with localized disease; they do not necessarily apply to younger men at higher risk. Younger men with stage T1a tumors have a longer projected period of risk than older men with the same stage of the disease and are therefore candidates for a potentially curative treatment. In studies of watchful waiting, the high rates of disease progression (34%–80%) indicate that few clinically evident prostate cancers are dormant.

BRIEF SUMMARY OF THE INVENTION

The present invention relates to novel benzopyran derivatives of formula (I):

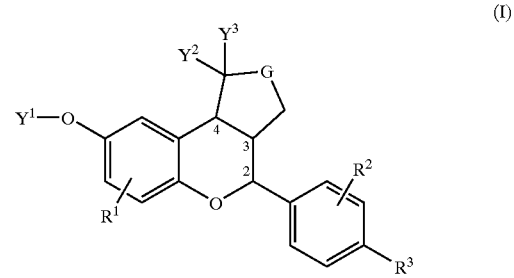

wherein $R_1$ and $R_2$ are each independently —H, $C_1$–$C_6$ alkyl, —OH, $C_1$–$C_6$ alkoxy, halo, or —$CF_3$;

$R_3$ is —H, $C_1$–$C_6$ alkyl, halo, or —$CF_3$;

$Y_1$, $Y_2$, and $Y_3$ are each independently —H or $C_1$–$C_6$ alkyl; and G is —$CH_2$—, —$CH_2$—$CH_2$—, or —$CH_2$—$CH_2$—$CH_2$—;

with the proviso that when G is —$CH_2$— and $R_1$, $R_2$, $R_3$, $Y_2$, and $Y_3$ are all —H, then $Y_1$ cannot be methyl;

or a pharmaceutically acceptable salt thereof.

Compounds of the invention are the following:

a) (±)-2-phenyl-6-hydroxy-cyclopentyl[c]3,4-dihydro-2H-1-benzopyran b) (±)-2-(4-fluorophenyl)-6-hydroxy-cyclopentyl[c]3,4-dihydro-2H-1-benzopyran c) (±)-2-(4-ethylphenyl)-6-hydroxy-cyclopentyl[c]3,4-dihydro-2H-1-benzopyran d) (±)-2-(4-trifluoromethylphenyl)-6-hydroxy-cyclopentyl[c]3,4-dihydro-2H-1-benzopyran e) (±)-2-(3-hydroxyphenyl)-6-hydroxy-cyclopentyl[c]3,4-dihydro-2H-1-benzopyran f) (±)-2-(4-methylphenyl)-6-hydroxy-cyclopentyl[c]3,4-dihydro-2H-1-benzopyran In a second embodiment, the present invention provides a pharmaceutical composition comprising a therapeutically effective amount of a compound of formula (I) and a pharmaceutically acceptable carrier.

In a further embodiment, the present invention provides medical methods of employing compounds of formula (I) as agonists of estrogen receptor ER beta, further utilized for the treatment of estrogen receptor ER beta-mediated diseases such as prostate cancer, benign prostatic hyperplasia, testicular cancer, cardiovascular diseases, neurodegenerative disorders, urinary incontinence, central nervous system (CNS) conditions, gastrointestinal (GI) tract conditions, and osteoporosis.

DETAILED DESCRIPTION OF THE INVENTION

As used in this application:
a) the term "halogen" refers to a fluorine atom, chlorine atom, bromine atom, or iodine atom;
b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, sec butyl, t-butyl, pentyl, hexyl, etc.;
c) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, sec-butoxy, t-butoxy, pentoxy, hexoxy, etc;
d) the designation "⁓" refers to a bond for which the stereochemistry is not designated;
e) the designation "◄" refers to a bond that protrudes forward out of the plane of the page;
f) the designation "⋯" refers to a bond that protrudes backward out of the plane of the page;
g) as used in the preparations and examples the following terms have the indicated meanings; "ng" refers to nanograms; "μg" refers to micrograms; "mg" refers to milligrams; "g" refers to grams; "kg" refers to kilograms; "nmole" refers to nanomoles; "mmol" refers to millimoles; "mol" refers to moles; "μL" refers to microliters; "mL" refers to milliliters; "L" refers to liters; "$R_f$" refers to retention factor; "° C." refers to degrees Celsius; "bp" refers to boiling point; "mm of Hg" refers to pressure in millimeters of mercury; "mp" refers to melting point; "dec" refers to decomposition; "$[\alpha]_D^{20}$" refer to specific rotation of the D line of sodium at 20° C. obtained in a 1 decimeter cell; "c" refers to concentration in g/mL; "nM" refers to nanomolar; "μM" refers to micromolar; "mM" refers to millimolar; "M" refers to molar; "$K_i$" refers to inhibiton constant; "$K_d$" refers to dissociation constant; "psi" refers to pounds per square inch; "rpm" refers to revolutions per minute; "HPLC" refers to high performance liquid chromatography; "HRMS" refers to high resolution mass spectrum; "THF" refers to tetrahydrofuran; "brine" refers to a saturated aqueous solution of sodium chloride; "L.O.D." refers to loss on drying; "μCi" refers to microcuries; "i.p." refers to intraperitoneally; "i.v." refers to intravenously; and "DPM" refers to disintegrations per minute;
h) by the designation

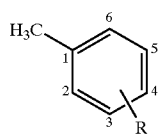

it is understood that the methyl is attached at the 1-position and the substituent or substituents represented by R can be attached in any of the 2, 3, 4, 5, or 6 positions;

i) the designation

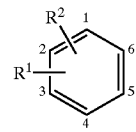

refers to a phenyl or substituted phenyl and it is understood that either substituent can be attached at any one of positions 1, 2, 3, 4, 5, or 6. It is further understood that when one of the substituents is attached at the 1-position the other substituent represented by R can be attached in any of the 2, 3, 4, 5, or 6 positions, that when one of the substituents is attached at the 2-position the other substituent represented by R can be attached in any of the 1, 3, 4, 5, or 6 positions, that when one of the substituents is attached at the 3-position the other substituent represented by R can be attached in any of the 1, 2, 4, 5, or 6 positions, that when one of the substituents is attached at the 4-position the other substituent represented by R can be attached in any of the 1, 2, 3, 5, or 6 positions, that when one of the substituents is attached at the 5-position the other substituent represented by R can be attached in any of the 1, 2, 3, 4, or 6 positions, and that when one of the substituents is attached at the 6-position the other substituent represented by R can be attached in any of the 1, 2, 3, 4, or 5 positions;

j) the numbering system and naming of the tricyclic ring system of formula (I) is as follows:
where G is —CH2—

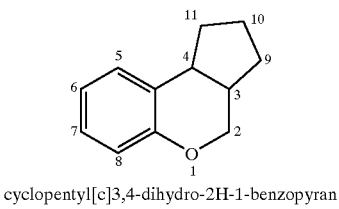

cyclopentyl[c]3,4-dihydro-2H-1-benzopyran where G is —CH2—CH2—

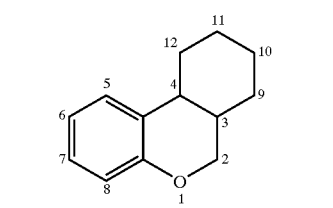

cyclohexyl[c]3,4-dihydro-2H-1-benzopyran where G is —CH2—CH2—CH2—

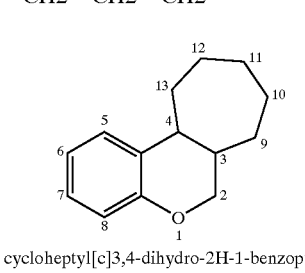

cycloheptyl[c]3,4-dihydro-2H-1-benzopyran j) the term "enantiomeric excess" or "ee" refers to the percent by which one enantiomer, E1, is in excess in a mixture of the two enantiomers, E1 plus E2, such that $\{(E1-E2) \div (E1+E2)\} \times 100 = ee$;

The compounds used in the method of the present invention may have one or more asymmetric centers. As a consequence of these chiral centers, the compounds of the present invention occur as racemates and as individual enantiomers, as well as diastereomers and mixtures of diastereomers. All asymmetric forms, individual isomers and combinations thereof, are within the scope of the present invention. The three main chiral centers, signified as 2, 3, and 4, are illustrated in formula (I).

The preferred relative stereochemistry of compounds of formula (I) is when chiral centers 2, 3, and 4 are all in the cis-configuration, as demonstrated by formulae IB and IC below:

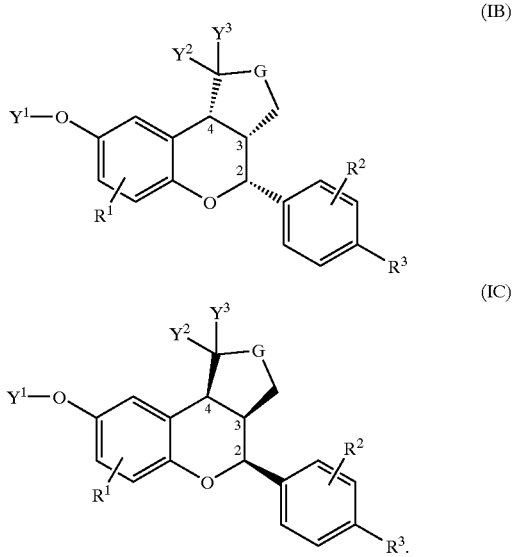

For the purpose of this invention, a compound designated "IB racemic" or "IC racemic", or their structure, indicates a racemic structure of compounds IB and IC. Also, for the purpose of this invention, a compound designated "ID racemic" or "IE racemic", or their structure as shown below, indicates a racemic structure of compounds ID and IE.

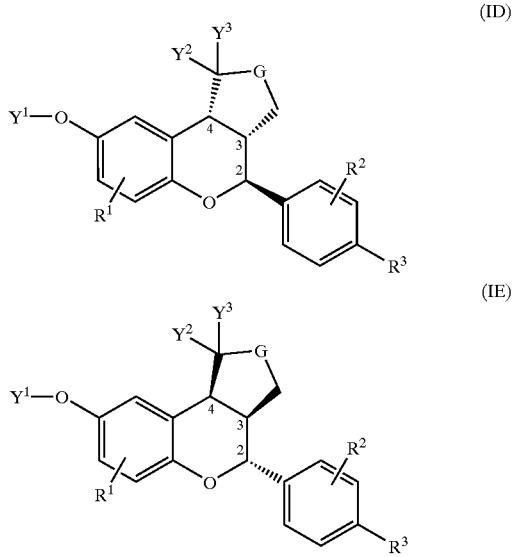

In order to preferentially prepare one optical isomer over its enantiomer, a number of routes are available. As an example, a mixture of enantiomers may be prepared, and then the two enantiomers may be separated. A commonly employed method for the separation of a racemic mixture is the use of chiral high pressure liquid chromatography. Further details regarding resolution of enantiomeric mixtures may be found in J. Jacques, et al., Enantiomers, Racemates, and Resolutions, (1991). "The term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by formula (I). Illustrative inorganic acids that form suitable salts include hydrochloric, hydrobromic, sulphuric, and phosphoric acid and acid metal salts such as sodium monohydrogen orthophosphate, and potassium hydrogen sulfate. Illustrative organic acids that form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (I). Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di- basic salts can be formed with those compounds.

Preferred embodiments of formula (I) are provided below:

(1) Compounds in which the chiral centers designated as 2, 3, and 4 are all in the cis-position;
(2) Compounds in which G is —CH$_2$— are preferred;
(3) Compounds in which Y$^2$ and Y$^3$ are both —H are preferred;
(4) Compounds in which R$^2$ is —H or —OH are preferred;
(5) Compounds in which R$^1$ is —H are preferred;
(6) Compounds in which Y$^1$ is —H are preferred;
(7) Compounds in which R$^3$ is —H, methyl, ethyl, fluoro, or —CF$_3$ are preferred.

It is understood that further preferred embodiments of formula (I) can be selected by requiring one or more of the preferred embodiments above. For example, the limitations of (1) can be combined with the limitations of (2); the limitations of (3) can be combined with the limitations of (4); the limitations of (1), (2), (3), (5), (6), and (7) can be combined; and the like.

Illustrative examples of the compounds encompassed by the present invention include the racemic mixtures and specific enantiomers of the following compounds:

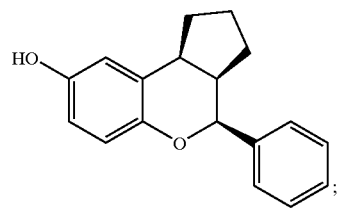

-continued
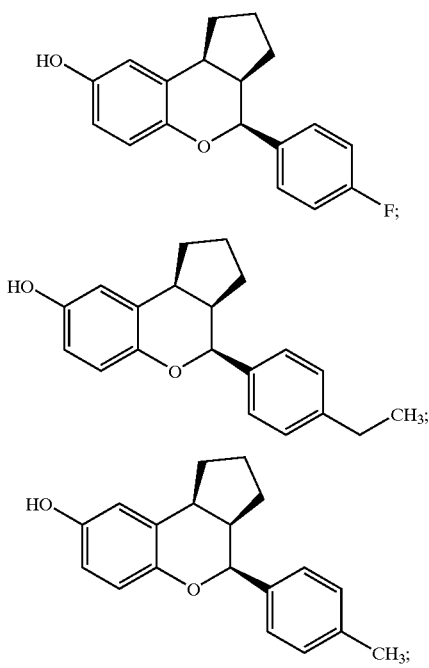
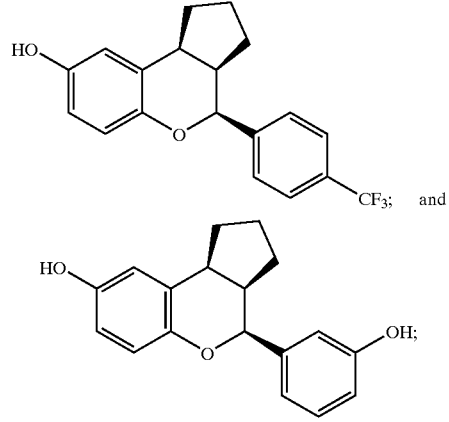
Reaction Schemes
Compounds of formula (I) and intermediates thereof can be prepared as described in Reaction Schemes A through D below. All substituents, unless otherwise indicated, are previously defined. The reagents and starting materials are readily available to one of ordinary skill in the art.
SCHEME A
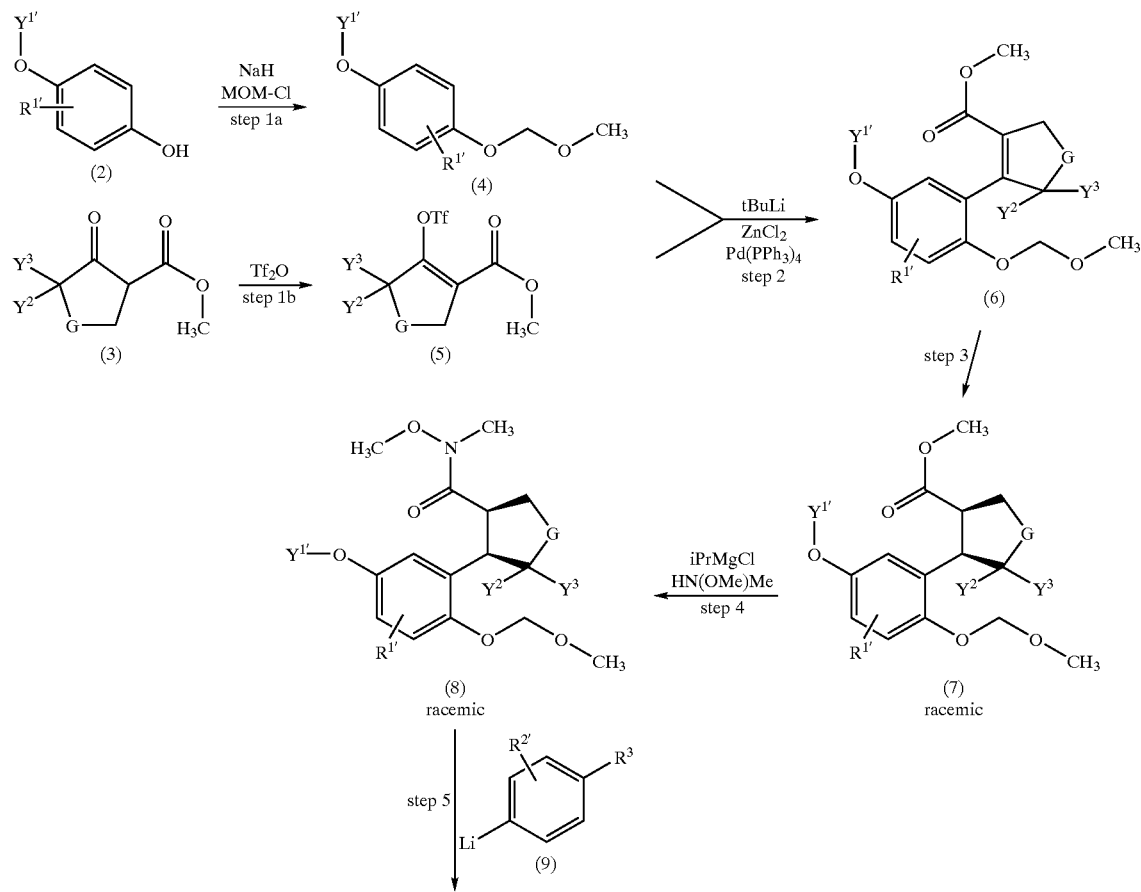

-continued

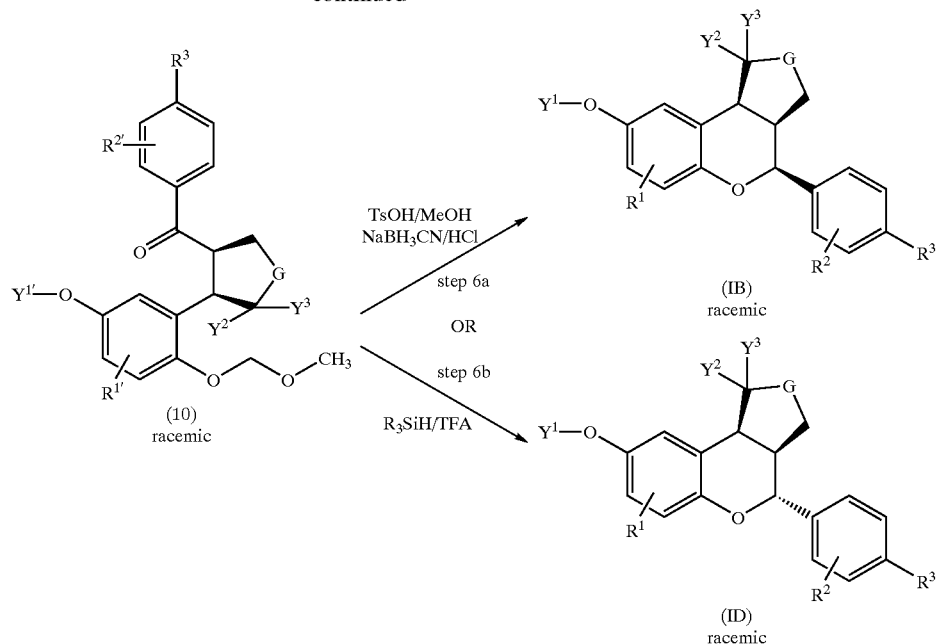

As used herein, $R^{1'}$, $R^{2'}$, and $Y^{1'}$ correspond to the substituents $R^1$, $R^2$, and $Y^1$, respectively, except for when the $R^1$ and $R^2$ substituents would be hydroxy and the $Y^1$ substituent would be —H (making the —O—$Y^1$ group a hydroxy). In these cases, the corresponding hydroxy group is protected with an alkoxymethylether, such as methoxymethyl ("MOM") or methoxyethoxymethyl ("MEM").

In reaction Scheme A, step 1a, the hydroxy groups on the phenol of formula (2) are protected with a suitable protecting group to provide the protected phenol of formula (4) utilizing techniques and procedures well know to one of ordinary skill in the art. For example, the phenol of formula (2) is combined with a suspension comprising a suitable anhydrous solvent such as anhydrous dimethylform-amide (DMF) and a suitable strong base such as a metal hydride, most preferably sodium hydride. To this suspension is added an amount of alkoxymethyl ether, preferably MOM, which corresponds to a roughly equimolar amount depending on the number of hydroxy groups to be protected on the phenol of formula (2). The reaction may be conducted at room temperature for a time ranging from about 30 minutes to about 2 days. The reaction is then quenched with water and an appropriate ether, such as diethyl ether, and the organic layer is washed with an appropriate base, such as sodium hydroxide, and brine. The protected phenol of formula (4) may be isolated and purified by techniques well known in the art, such as extraction, evaporation, trituration, chromatography, and recrystallization.

In Scheme A, step 1b, a 2-oxocycloalkanecarboxylate of formula (3) is activated via the triflate to provide the activated cycloalkane carboxylate of formula (5) utilizing procedures and techniques well known in the art; G. T. Crisp et al., *J. Org. Chem.* 57, 6972–6975 (1992). For example, a methyl-2-oxocycloalkanecarboxylate of formula (3) is dissolved under anhydrous conditions in a suitable solvent, such as tetrahydrofuran, dichloromethane, acetone, ethyl acetate, toluene, or diethyl ether and contacted with a suitable activating agent such as triflic anhydride. The reaction is carried out in the presence of a base, such as N-methylmorpholine, sodium carbonate, triethylamine, N,N-diisopropylethylamine, potassium carbonate or sodium bicarbonate. The reaction is generally carried out at temperatures of from −78° C. to ambient temperature. Generally, the reactions require 1 to 24 hours. The reaction may then be quenched. The product of formula (5) can be isolated and purified by techniques well known in the art, such as extraction, evaporation, trituration, chromatography, and recrystallization.

In Scheme A, step 2, the protected phenol of formula (4) is coupled with the activated cycloalkane carboxylate of formula (5) to provide the coupled product of formula (6). For example, the coupling reaction is conducted in the presence of butyllithium, zinc chloride and a Pd species. The reaction is preferably carried out in a suitable solvent such as tetrahydrofuran (THF), and may initially be carried out under anhydrous conditions. Preferably, the protected phenol of formula (4) is dissolved in a suitable solvent such as THF, treated with butyllithium at reduced temperature, zinc chloride in solvent is then added and the temperature allowed to rise to ambient. The palladium species, such as tetrakis(triphenylphosphine)Pd(0), is added together with the activated cycloalkane carboxylate of formula (5) and the temperature is preferably raised to the reflux temperature of the solvent for a period of time ranging from about 6 to 24 hours. The coupled product of formula (6) can be isolated and purified by techniques well known in the art, such as extraction, evaporation, trituration, chromatography, and recrystallization.

In Scheme A, step 3, the coupled product of formula (6) is reduced with a suitable reducing agent to provide the reduced product of formula (7) utilizing techniques and procedures well known in the art. For example, the coupled product of formula (6) is contacted with a suitable reducing agent, such as a palladium species, preferably 5% carbon on palladium, in a suitable solvent or solvent mixture, such as methanol. The reaction is preferably carried out in the presence of a suitable base, such as a trialkylamine, more preferably, triethylamine. The reaction mixture is then heated to a temperature ranging from about 30° C. to about reflux for a period of time ranging from about 2 to 24 hours.

The reduced product of formula (7) can be isolated and purified by techniques well known in the art, such as extraction, evaporation, trituration, chromatography, and recrystallization.

In Scheme A, step 4, the reduced product of formula (7) can be converted to the Weinreb-amide of formula (8). This reaction can be performed utilizing a reactin of the type described by J. M. Williams, et al., *Tetrahedron Letters* 36, 5461–5464 (1995). For example, the reduced product of formula (7) is combined with N,O-dimethylhydroxylamine hydrochloride in a suitable aprotic solvent, such as tetrahydrofuran, preferably under anhydrous conditions and cooled to a temperature ranging from about 0° C. to about −30° C., more preferably about −10° C. A suitable Grignard reagent, preferably isopropyl magnesium chloride, is then added in a molar ratio of about 1.5 and reaction mixture is stirred for about 15 minutes to 2 hours. The reaction is then quenched with a proton source such as, for example, saturated ammonium chloride. The Weinreb-amide of formula (8) can be isolated and purified by techniques well known in the art, such as extraction, evaporation, trituration, chromatography, and recrystallization.

to that described by A. Srikrishna, et. Al., Tetrahedron, vol. 51, no. 11, pp. 3339–3344, 1995. Methanol saturated with hydrochloric acid is then slowly added until a yellow color is maintained. The reaction is stirred for about 1 to 2 hours past the point of final color change. The reaction is then quenched with a suitable proton acceptor, such as saturated sodium bicarbonate. This set of reaction conditions for step 6a will result in a cis-configuration of the chiral centers (e.g., those compounds in IB or IC). The R3SiH/TFA conditions of step 6b will result in a trans-configuration of the chiral centers (e.g., those compounds in ID or IE). The product of formula (IA) or (IA') can then be isolated and purified by techniques well known in the art, such as extraction, evaporation, trituration, chromatography, and recrystallization.

Alternatively, the coupled product of formula (6) may be synthesized as described in reaction Scheme B. All substituents, unless otherwise indicated, are previously defined. The reagents and starting materials are readily available to one of ordinary skill in the art.

SCHEME B

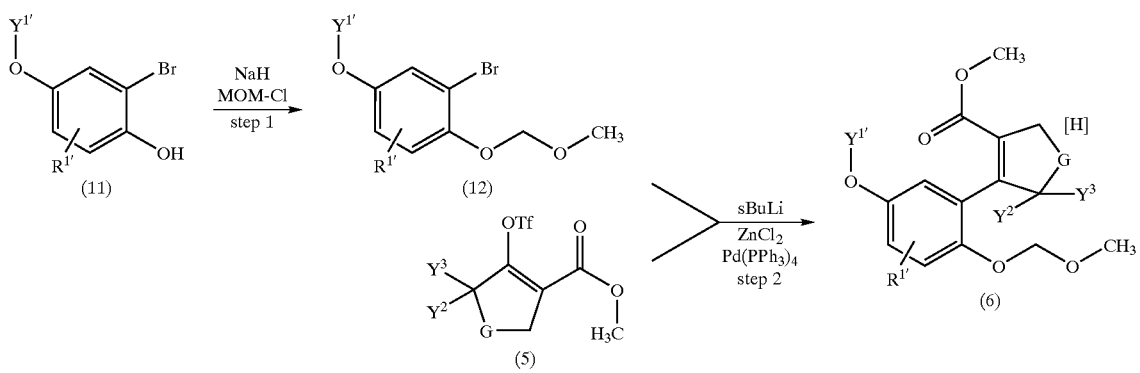

In Scheme A, step 5, the Weinreb-amide of formula (8) is combined with the aryl lithium of formula (9) to form the ketone of formula (10). For example, the aryl lithium of formula (9) is added to a solution of Weinreb-amide of formula (8) in a suitable aprotic solvent, such as anhydrous THF, cooled to a temperature ranging from about −20° C. to about 5° C., preferably 0° C., and stirred for a period of time ranging from about 15 minutes to 3 hours. The reaction is then quenched with a proton source, such as, for example, saturated sodium bicarbonate. The ketone of formula (10) can be isolated and purified by techniques well known in the art, such as extraction, evaporation, trituration, chromatography, and recrystallization.

In Scheme A, step 6a or 6b, the ketone of formula (10) is subjected to an acid-catalyzed cyclization followed by reduction of the resulting hemiketal to provide a compound of formula (IA or IA'), which represents the racemic mixture of a compound of formula (I). For example, in step 6a, p-toluenesulfonic acid is added in roughly equimolar proportions to the ketone of formula (10) in a suitable alcohol solvent, such as anhydrous methanol. The mixture is then heated at temperature ranging from 40° C. to 60° C., preferably 50° C., for a period of time ranging from 12 to 24 hours, preferably 18 hours. The reaction is then cooled to ambient temperature and a suitable reducing agent, such as sodium cyanoborohydride, is added along with a suitable indicator such as bromocreosol green in a procedure similar In Scheme B, step 1, the hydroxy groups on the bromophenol of formula (11) are protected with a suitable protecting group to provide the protected bromophenol of formula (12) utilizing techniques and procedures as set forth in Scheme A, step 1a.

In Scheme B, step 2, the protected bromophenol of formula (12) is coupled with the activated cycloalkane carboxylate of formula (5) to provide the coupled product of formula (6) according the techniques and procedures set forth in Scheme A, step 2.

An alternative method for providing specific bromo-substituted intermediates are provided in Scheme C.

SCHEME C

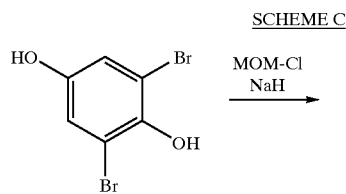

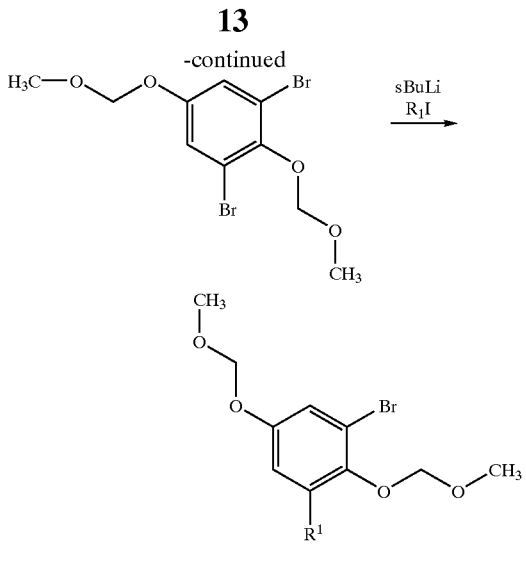

The following examples are presented to further illustrate the preparation of compounds of the present invention. It is not intended that the invention be limited in scope by reason of any of the following examples.

PREPARATION 1

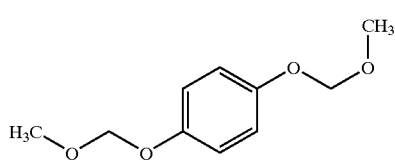

Stir a suspension of sodium hydride (60% in mineral oil, 3.81 g, 95.45 mmol) in anhydrous DMF (50 mL) under nitrogen atmosphere at 0° C. and add a solution of hydroquinone (5.00 g, 45.45 mmol) in anhydrous DMF (50 mL) dropwise. Add to this suspension methoxymethyl chloride (7.2 mL, 95.45 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield the title compound (5.64 g, 63%) as a clear oil. $^1$H NMR (CDCl$_3$): 6.97 (s, 4H), 5.11 (s, 4H), 3.47 (s, 6H).

PREPARATION 2

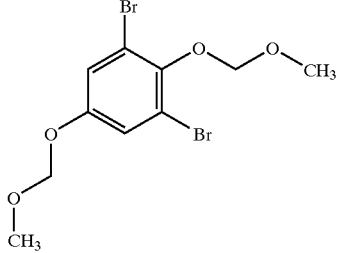

Stir a suspension of sodium hydride (60% in mineral oil, 1.58 g, 39.21 mmol) in anhydrous DMF (50 mL) under nitrogen atmosphere at 0° C. and add a solution of 2,6-dibromohydroquinone (5.00 g, 18.67 mmol) in anhydrous DMF (50 mL) dropwise. Add to this suspension methoxymethyl chloride (3.0 mL, 39.21 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield the title compound (3.49 g, 53%) as a clear oil. $^1$H NMR (CDCl$_3$): 7.23 (s,2H), 5.10 (s, 4H), 3.46 (s, 6H).

PREPARATION 3

Stir a suspension of sodium hydride (60% in mineral oil, 3.00 g, 74.92 mmol) in anhydrous DMF (50 mL) under nitrogen atmosphere at 0° C. and add a solution of methoxyhydroquinone (5.00 g, 35.67 mmol) in anhydrous DMF (50 mL) dropwise. Add to this suspension methoxymethyl chloride (5.2 mL, 74.92 mmol) dropwise with additional gas evolution noted. Allow the reaction to warm to ambient temperature and stir for one hour. Quench the reaction with water and add diethyl ether. Wash the organic layer with 1N sodium hydroxide and brine. Dry the organic layer over sodium sulfate, concentrate in vacuo, and flash chromatograph with 20% ethyl acetate/hexane to yield the title compound (5.84 g, 72%) as a clear oil. $^1$H NMR (CDCl$_3$): 7.05 (d, J=8.6, 1H), 6.63 (d, J=2.7, 1H), 6.55 (dd, J=9.0, 2.7, 1H), 5.14 (s, 2H), 5.12 (s, 2H), 3.86 (s, 3H), 3.51 (s, 3H), 3.47 (s, 3H).

PREPARATION 4

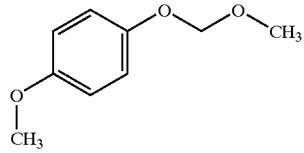

Stir a suspension of sodium hydride (60% in mineral oil, 3.54 g, 88.61 mmol) in anhydrous DMF (100 mL) under nitrogen atmosphere at 0° C. and add a solution of 4-methoxyphenol (10.00 g, 80.55 mmol) in anhydrous DMF (50 mL) dropwise. Add to this suspension methoxymethyl chloride (6.7 mL, 88.61 mmol) dropwise. Allow the reaction to warm to ambient temperature and stir for one hour. Quench the reaction with water and add diethyl ether. Wash the organic layer with 1 N sodium hydroxide and brine. Dry the organic layer over sodium sulfate, concentrate in vacuo, and flash chromatograph with 20% ethyl acetate/hexane to yield the title compound (11.55 g, 85%) as a clear oil.

PREPARATION 5

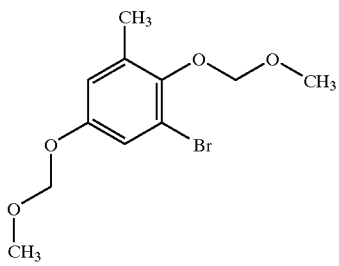

Cool a solution of Preparation 2 (1.00 g, 2.81 mmol) to −78° C. and add s-BuLi (1.3 M in cylcohexane, 2.10 mL, 2.81 mmol) dropwise. Stir the solution for 15 minutes, then add methyl iodide (0.18 mL, 2.81 mmol) and stir overnight, allowing to warm to ambient temperature. Quench with saturated sodium bicarbonate and add ethyl acetate. Wash with brine, dry the organic layer over sodium sulfate, concentrate in vacuo, and flash chromatograph with 10% ethyl acetate/hexane to yield the title compound (0.66 g, 81%) as a clear oil. $^1$H NMR (CDCl$_3$): 7.12 (d, J=2.9, 1H), 6.83 (d, J=2.9, 1H), 5.10 (s, 2H), 5.04 (s, 2H), 3.63 (s, 3H), 3.48 (s, 3H), 2.30 (s, 3H). MS calcd 291.1; MS (M+1) 291.2, 293.2.

PREPARATION 6

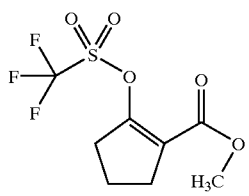

This preparation was followed according to J. Org. Chem. 57, 1992, 6972–6975. Stir a solution of methyl 2-oxocylcopentanecarboxylate (10.0 g, 70.42 mmol) in anhydrous dichloromethane (300 mL) cooled to −78° C. and add diisopropylethylamine (61.5 mL, 352.1 mmol) and triflic anhydride (14.2 mL, 84.51 mmol). Stir the reaction was stir for 16 hours, allowing it to warm to ambient temperature. Quench the reaction with water and wash with 10% citric acid followed by brine. Dry the organic layer over sodium sulfate, concentrate in vacuo, and flash chromatograph with 15% ethyl acetate/hexane to yield the title compound (12.0 g, 63%) as a dark oil which is used without further purification. $^1$H NMR (CDCl$_3$): 3.79 (s, 3H), 2.75–2.68 (m, 4H), 2.03–15 1.98 (m, 2H).

PREPARATION 7

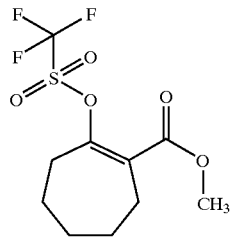

Using a method similar to the preparation of Preparation 6, with an exception of using methyl 2-oxo-1-cycloheptanecarboxylate (5.00 g, 29.37 mmol) to yield the title compound (4.34 g, 49%) as a dark oil.

PREPARATION 8

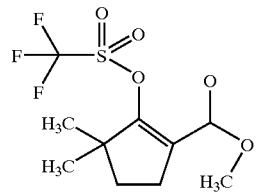

Stir a solution of methyl 2-oxo-5,5-dimethyl-cyclopentanecarboxylate (J. Chem. Soc., 1996, 1539–1540) (0.85 g, 5.00 mmol) in anhydrous dichloromethane (15 mL) cooled to −78° C. and add diisopropylethylamine (4.4 mL, 25.00 mmol) and triflic anhydride (1.0 mL, 6.00 mmol). Stir the reaction was stir for 16 hours, allowing it to warm to ambient temperature. Quench the reaction with water and wash with 10% citric acid followed by brine. Dry the organic layer over sodium sulfate, concentrate in vacuo, and flash chromatograph with 15% ethyl acetate/hexane to yield the title compound (1.16 g, 77%) as a dark oil which is used without further purification. $^1$H NMR (CDCl$_3$): 3.78 (s, 3H), 2.64 (t, J=7.1, 2H), 1.83 (t, J=7.1, 2H), 1.18 (s, 6H).

PREPARATION 9

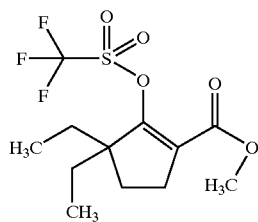

Stir a solution of methyl 2-oxo-5,5-diethyl-cyclopentanecarboxylate (J. Chem. Soc., 1996, 1539–1540) (2.94 g, 14.85 mmol) in anhydrous dichloromethane (100 mL) cooled to −78° C. and add diisopropylethylamine (13.0 mL, 74.25 mmol) and triflic anhydride (3.0 mL, 17.82 mmol). Stir the reaction was stir for 16 hours, allowing it to warm to ambient temperature. Quench the reaction with water and wash with 10% citric acid followed by brine. Dry the organic layer over sodium sulfate, concentrate in vacuo, and flash chromatograph with 15% ethyl acetate/hexane to yield the title compound (3.96 g, 82%) as a dark oil which is used without further purification. $^1$H NMR (CDCl$_3$): 3.78 (s, 3H), 2.60 (t, J=7.4, 7.8, 2H), 1.83 (t, J=7.8, 7.1, 2H), 1.46 (q, J=7.4, 7.4, 7.4, 4H), 0.91 (t, J=7.4, 7.4, 6H).

PREPARATION 10

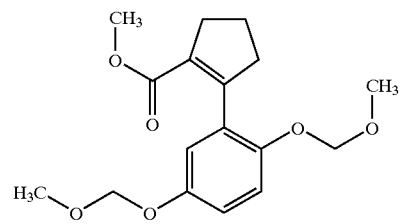

Cool a solution of Preparation 1 (0.95 g, 4.81 mmol) in anhydrous THF (25 mL) to −78° C. and add t-BuLi (1.7M in pentane, 2.8 mL, 4.81 mmol). Stir the solution 15 minutes, then warm to 0° C. Add a solution of zinc chloride (1.0 M in diethyl ether, 4.8 mL, 4.81 mmol) dropwise and allow the resulting solution to warm to ambient temperature. Cannulate this solution into a solution of Preparation 6 (0.88 g, 3.21 mmol) and tetrakis(triphenylphosphine)Pd(0) (0.37 g, 0.32 mmol) in anhydrous THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 30% ethyl acetate/hexane to yield the title compound (0.56 g, 55%) as a clear oil. $^1$H NMR (CDCl$_3$): 7.04 (d, J=9.0, 1H), 6.90 (dd, J=3.1, 9.0, 1H), 6.81 (d, J=3.1, 1H), 5.10 (s, 2H), 5.02 (s, 2H), 3.56 (s, 3H), 3.46 (s, 3H), 3.42 (s, 3H), 2.80 (t, J=8.6, 8.2, 4H), 2.05–1.95 (m, 2H). MS calcd 322.2; MS (M+1) 323.1.

PREPARATION 11

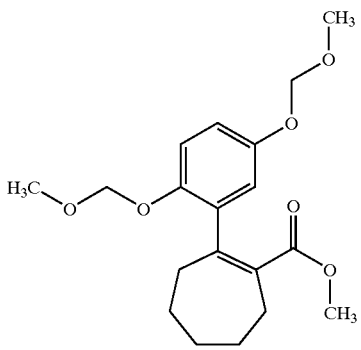

Cool a solution of Preparation 1 (2.00 g, 10.13 mmol) in anhydrous THF (25 mL) to −78° C. and add t-BuLi (1.7M in pentane, 5.9 mL, 10.13 mmol). Stir the solution 15 minutes, then warm to 0° C. Add a solution of zinc chloride (1.0 M in diethyl ether, 10.1 mL, 10.13 mmol) dropwise and allow the resulting solution to warm to ambient temperature. Cannulate this solution into a solution Preparation 7 (2.04 g, 6.75 mmol) and tetrakis(triphenylphosphine)Pd(0) (0.40 g, 0.34 mmol) in anhydrous THF (25 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield the title compound (2.13 g, 90%) as a colorless oil. $^1$H NMR (CDCl$_3$): 6.98 (d, J=9.0, 1H, 6.85 (dd, J=3.1, 9.0, 1H), 6.65 (d, J=3.1, 1H), 5.10 (s, 4H), 3.45 (s, 3H), 3.44 (s, 3H), 3.38 (s, 3H), 2.56–2.50 (m, 4H), 1.84–1.80 (m, 2H), 1.65–1.60 (m, 4H). MS calcd 350.1; MS (M+1) 351.1.

PREPARATION 12

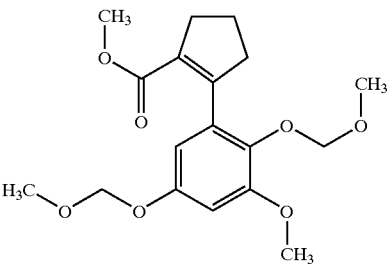

Cool a solution of Preparation 3 (2.18 g, 9.56 mmol) in anhydrous THF (40 mL) to −78° C. and add t-BuLi (1.7M in pentane, 6.2 mL, 10.52 mmol). Stir the solution 15 minutes, then warm to 0° C. Add a solution of zinc chloride (1.0 M in diethyl ether, 9.6 mL, 9.56 mmol) dropwise and allow the resulting solution to warm to ambient temperature. Cannulate this solution into a solution of Preparation 6 (2.62 g, 9.56 mmol) and tetrakis(triphenylphosphine)Pd(0) (0.55 g, 0.48 mmol) in anhydrous THF (40 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield the title compound (0.62 g, 18%) as a colorless oil. $^1$H NMR (CDCl$_3$): 6.57 (d, J=2.7, 1H), 6.40 (d, J=2.7, 1H), 5.11 (s, 2H), 4.89 (s, 2H), 3.81 (s, 3H), 3.58 (S, 3H), 3.47, (s, 3H), 3.44 (s, 3H), 2.83–2.77 (m, 4H), 2.03–1.96 (m, 2H). MS calcd 352.1; MS (M+1) 353.1.

PREPARATION 13

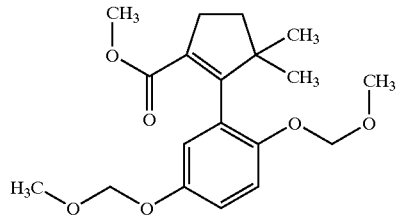

Cool a solution of Preparation 1 (1.13 g, 5.71 mmol) in anhydrous THF (40 mL) to −78° C. and add t-BuLi (1.7M in pentane, 3.4 mL, 5.71 mmol). Stir the solution 15 minutes, then warm to 0° C. Add a solution of zinc chloride (1.0 M in diethyl ether, 5.7 mL, 5.71 mmol) dropwise and allow the resulting solution to warm to ambient temperature. Cannulate this solution into a solution of Preparation 8 (1.15 g, 3.80 mmol) and tetrakis(triphenylphosphine)Pd(0) (0.55 g, 0.48 mmol) in anhydrous THF (40 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 15% ethyl acetate/hexane to yield the title compound (0.42 g, 32%) as a colorless oil. $^1$H NMR (CDCl$_3$): 7.05 (d, J=9.0, 1H), 6.92 (dd, J=3.1, 9.0, 1H), 6.62 (d, J=3.1, 1H), 5.11 (S, 2H), 5.01 (s, 2H), 3.49 (s, 3H), 3.46 (s, 3H), 3.40 (s, 3H), 2.70 (t, J=7.0, 7.4, 2H), 1.86 (t, J=7.4, 7.0, 2H), 1.59 (bs, 6H). MS calcd 350.1; MS (M+1) 351.1.

PREPARATION 14

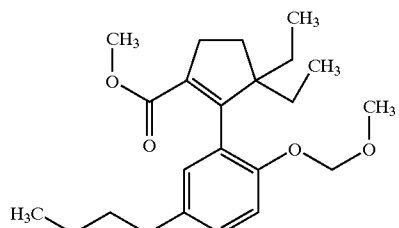

Cool a solution of Preparation 1 (3.64 g, 18.38 mmol) in anhydrous THF (50 mL) to −78° C. and add t-BuLi (1.7M in pentane, 3.4 mL, 5.71 mmol). Stir the solution 15 minutes, then warm to 0° C. Add a solution of zinc chloride (1.0 M in diethyl ether, 10.8 mL, 18.38 mmol) dropwise and allow the resulting solution to warm to ambient temperature. Cannulate this solution into a solution of Preparation 9 (3.96 g, 12.25 mmol) and tetrakis(triphenylphosphine)Pd(0) (0.71 g, 0.61 mmol) in anhydrous THF (50 mL) and heat the resulting solution to 50 C for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 15% ethyl acetate/hexane to yield the title compound (3.30 g, 84%) as a colorless oil. $^1$H NMR (CDCl$_3$): 7.05 (d, J=9.0, 1H), 6.89 (dd, J=3.1, 9.0, 1H), 6.62 (d, J=2.7, 1H), 5.11 (s, 2H), 5.00 (s, 2H), 3.49 (s, 3H), 3.46 (s, 3H), 3.40 (s, 3H), 2.65 (bt, J=7.8, 7.0, 2H), 1.87 (t, J=7.8, 7.4, 2H), 1.45–1.38 (m, 4H), 0.90–0.82 (m, 6H). MS calcd 378.1; MS (M+1) 379.1.

PREPARATION 15

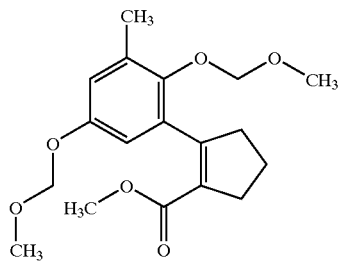

Cool a solution of Preparation 5 (1.24 g, 4.26 mmol) in anhydrous THF (20 mL) to −78° C. and add s-BuLi (1.3M in cyclohexane, 3.3 mL, 4.26 mmol). Stir the solution 15 minutes, then warm to 0° C. Add a solution of zinc chloride (1.0 M in diethyl ether, 4.3 mL, 4.26 mmol) dropwise and allow the resulting solution to warm to ambient temperature. Cannulate this solution into a solution of Preparation 6 (1.17 g, 4.26 mmol) and tetrakis(triphenylphosphine)Pd(0) (0.24 g, 0.21 mmol) in THF (20 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield the title compound (0.54 g, 38%) as a colorless oil. $^1$H NMR (CDCl$_3$): 6.80 (d, J=2.4, 1H), 6.61 (d, J=2.3, 1H), 5.09 (s, 2H), 4.79 (s, 2H), 3.57 (s, 3H), 3.48 (s, 3H), 3.46 (s, 3H), 2.83–2.76 (m, 4H), 2.29 (s, 3H), 2.02–1.96 (m, 2H). MS calcd 336.2; MS (M+1) 337.2.

PREPARATION 16

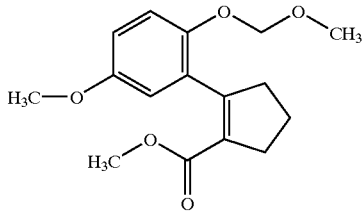

Cool a solution of Preparation 4 (2.00 g, 11.90 mmol) in anhydrous THF (20 mL) to −78° C. and add s-BuLi (1.3M in cyclohexane, 7.7 mL, 13.09 mmol). Stir the solution 15 minutes, then warm to 0° C. Add a solution of zinc chloride (1.0 M in diethyl ether, 11.9 mL, 11.90 mmol) dropwise and allow the resulting solution to warm to ambient temperature. Cannulate this solution into a solution of Preparation 6 (3.26 g, 11.90 mmol) and tetrakis(triphenylphosphine)Pd(0) (0.69 g, 0.58 mmol) in THF (20 mL) and heat the resulting solution to 50° C. for 16 hours. Cool the reaction to ambient temperature and quench with water. Add ethyl acetate and wash the resulting organic layer with saturated sodium bicarbonate and brine. Dry the organic layer over sodium sulfate, concentrate in vacuo, and flash chromatograph with 20% ethyl acetate/hexane to yield the title compound (1.28 g, 38%) as a colorless oil which is a mixture of regioisomers by $^1$H NMR. MS calcd 292.1; MS (M+1) 293.1.

PREPARATION 17

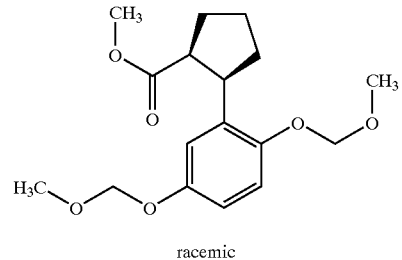

racemic

To a suspension of 5% palladium on carbon (0.27 g) in methanol (15 mL) add a solution of Preparation 10 (0.27 g, 0.84 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 30% ethyl acetate/hexane to yield the title compound (0.20 g, 75%) as a clear oil. $^1$H NMR (CDCl$_3$): 6.98 (d, J=8.6, 1H), 6.86 (d, J=3.1, 1H), 6.81 (dd, J=3.1, 9.0, 1H), 5.1 (s, 2H), 5.08 (s, 2H), 3.64–3.59 (m, 1H), 3.50 (s, 3H), 3.45 (s, 3H), 3.39–3.30 (m, 1H), 3.19 (s, 3H), 2.12–1.98 (m, 4H), 1.93–1.82 (m, 1H), 1.72–1.63 (m, 1H), MS calcd 324.2; MS (M+1) 325.2.

PREPARATION 18

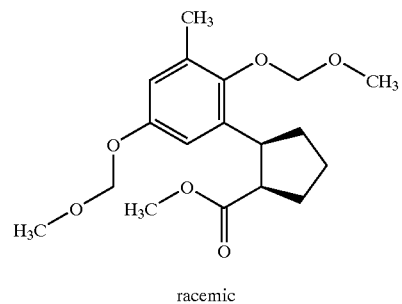

racemic

To a suspension of 5% palladium on carbon (0.25 g) in methanol (25 mL) add a solution Preparation 15 (0.54 g, 1.61 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield the title compound (0.49 g, 89%) as a clear oil. $^1$H NMR (CDCl$_3$): 6.69 (d, J=2.8, 1H), 6.65 (d, J=3.1, 1H), 5.04 (m, 2H), 4.93 (dd, J=5.9, 16.0, 2H), 3.73–3.67 (m, 1H), 3.57 (s, 3H), 3.42 (s, 3H), 3.25–3.19 (m, 4H), 2.25 (s, 3), 2.17–2.12 (m, 1H), 2.05–1.85 (m, 4H), 1.70–1.60 (m, 1H). MS calcd 338.2; MS (M+1) 339.2.

PREPARATION 19

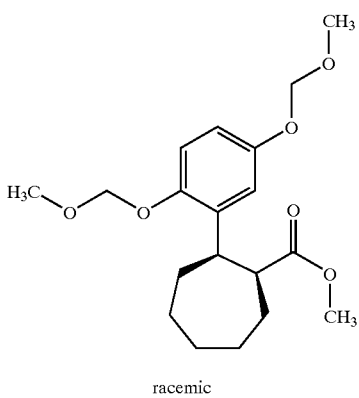

racemic

To a suspension of 5% palladium on carbon (0.38 g) in methanol (35 mL) add a solution of Preparation 11 (0.75 g, 2.14 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield the title compound (0.63 g, 84%) as a clear oil. $^1$H NMR (CDCl$_3$): 6.95 (d, J=9.0, 1H), 6.85 (d, J=3.1, 1H), 6.79 (dd, J=3.1, 9.0, 1H), 5.15 (s, 2H), 5.13–5.05 (m, 2H), 3.56–3.51 (m, 1H), 3.50 (s, 3H), 3.45 (s, 3H), 3.30 (s, 3H), 3.08–3.04 (m, 1H), 2.23–2.17 (m, 1H), 2.04–1.80 (m, 6H), 1.55–1.40 (m, 3H). MS calcd 352.2; MS (M+1) 353.2.

PREPARATION 20

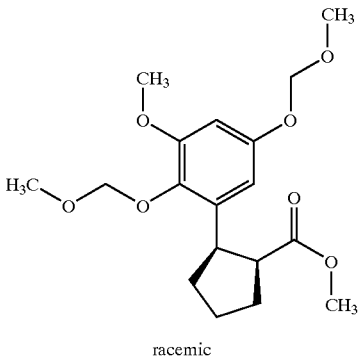

racemic

To a suspension of 5% palladium on carbon (0.08 g) in methanol (50 mL)/triethylamine (1.0 mL) add a solution of Preparation 12 (0.62 g, 1.76 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield the title compound (0.50 g, 81%) as a clear oil. $^1$H NMR (CDCl$_3$): 6.50 (d, J=2.7, 1H), 6.44 (d, J=2.7, 1H), 5.14–5.05 (m, 4H), 3.80 (m, 4H), 3.58 (s, 3H), 3.46 (s, 3H), 3.25 (m, 4H), 2.15–2.09 (m, 1H), 2.07–1.90 (m, 4H), 1.72–1.64 (m, 1H). MS calcd 354.1; MS (M+1) 355.1.

PREPARATION 21

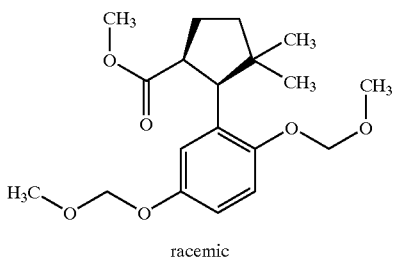

racemic

To a suspension of 5% palladium on carbon (0.05 g) in methanol (50 mL)/triethylamine (1.0 mL) add a solution of Preparation 13 (0.42 g, 1.19 mmol) in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 20% ethyl acetate/hexane to yield the title compound (0.16 g, 38%) as a clear oil. $^1$H NMR (CDCl$_3$): 7.00 (d, J=8.2, 0.5H), 6.94 (d, J=7.8, 0.5H), 6.84–6.75 (m, 1.5H), 6.67 (d, J=3.1, 0.5H), 5.12–5.01 (m, 4H), 3.77 (d, J=9.0, 0.5H), 3.64 (d, J=11.3, 0.5H), 3.52 (s, 1.5H), 3.49 (s, 1.5H), 3.48–3.43 (s, 4.5H), 3.35 (s, 1.5H), 2.55–2.42 (m, 0.5H), 2.17–2.02 (m, 1H), 1.95–1.88 (m, 0.5H), 1.81–1.75 (m, 1H), 1.69–1.60 (m, 0.5H), 1.55–1.50 (m, 0.5H), 1.15 (s, 1.5H), 1.01 (s, 1.5H), 0.78 (s, 3H). MS calcd 352.2; MS (M+1) 353.2.

PREPARATION 22

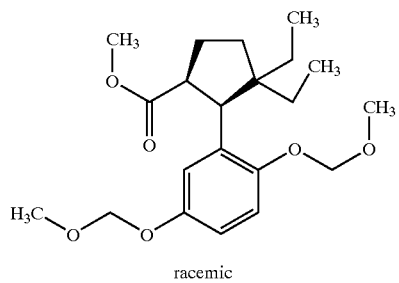

racemic

To a suspension of 5% palladium on carbon (0.58g) in methanol (50 mL)/triethylamine (1.0 mL) add a solution of Preparation 14 (1.25 g, 3.89 mmol)in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 15% ethyl acetate/hexane to yield the title compound (0.89 g, 72%) as a clear oil. MS calcd 380.2; MS (M+1) 381.2.

PREPARATION 23

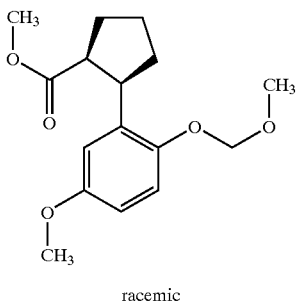

racemic

To a suspension of 5% palladium on carbon (0.15 g) in methanol (50 mL)/triethylamine (1.0 mL) add a solution of Preparation 14 (0.58 g, 1.80 mmol)in methanol (10 mL). Place the mixture on a Parr shaker under hydrogen (60 psi) at 40° C. for twelve hours. Purge the reaction with nitrogen and filter with celite. Concentrate the filtrate in vacuo and flash chromatograph with 15% ethyl acetate/hexane to yield the title compound (0.25 g, 43%) as a clear oil. MS calcd 294.1; MS (M+1) 295.1.

PREPARATION 24

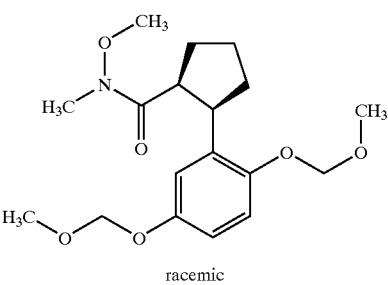

racemic

This preparation follows that in Tet Letters 36, 31, 1995, 5461–5464. Cool a suspension of Preparation 17 (0.50 g, 1.54 mmol) and N,O-dimethylhydroxylamine hydrochloride (0.23 g, 2.31 mmol) in anhydrous THF (25 mL) to −10° C. in an ice/acetone bath, add isopropyl magnesium chloride (2.0M, 2.3 mL, 4.62 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.49 g, 90%) as a clear oil which is used without further characterization.

PREPARATION 25

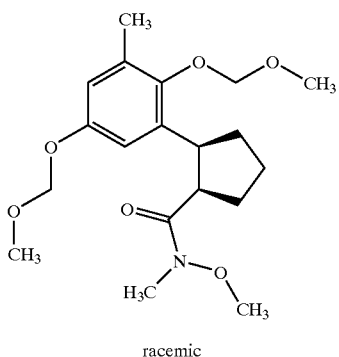

racemic

Cool a suspension of Preparation 18 (0.48 g, 1.42 mmol) and N,O-dimethylhydroxylamine hydrochloride (0.21 g, 2.13 mmol) in anhydrous THF (20 mL) to −10° C. in an ice/acetone bath, add isopropyl magnesium chloride (2.0M, 2.1 mL, 4.20 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.46 g, 88%) as a clear oil which is used without further characterization.

PREPARATION 26

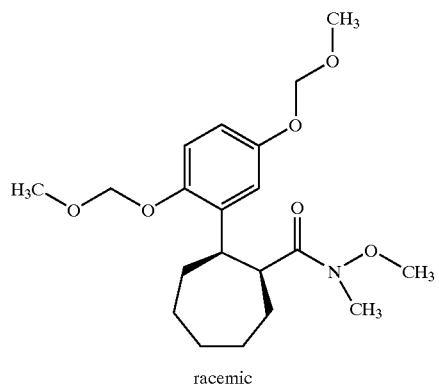

racemic

Cool a suspension of Preparation 19 (0.63 g, 2.53 mmol) and N,O-dimethylhydroxylamine hydrochloride (0.26 g, 2.68 mmol) in anhydrous THF (30 mL) to −10° C. in an ice/acetone bath, add isopropyl magnesium chloride (2.0M, 2.7 mL, 5.40 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.54 g, 76%) as a clear oil which is used without further characterization.

PREPARATION 27

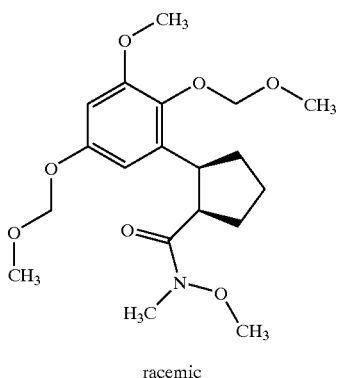

racemic

Cool a suspension of Preparation 20 (0.50 g, 1.41 mmol) and N,O-dimethylhydroxylamine hydrochloride (0.24 g, 2.12 mmol) in anhydrous THF (30 mL) to −10° C. in an ice/acetone bath, add isopropyl magnesium chloride (2.0M, 2.1 mL, 4.20 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.31 g, 57%) as a clear oil which is used without further characterization.

PREPARATION 28

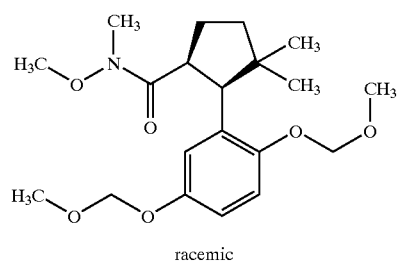

racemic

Cool a suspension of Preparation 21 (0.16 g, 0.45 mmol) and N,O-dimethylhydroxylamine hydrochloride (0.07 g, 0.68 mmol) in anhydrous THF (10 mL) to −10° C. in an ice/acetone bath, add isopropyl magnesium chloride (2.0M, 0.7 mL, 1.40 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.15 g, 87%) as a clear oil which is used without further characterization.

PREPARATION 29

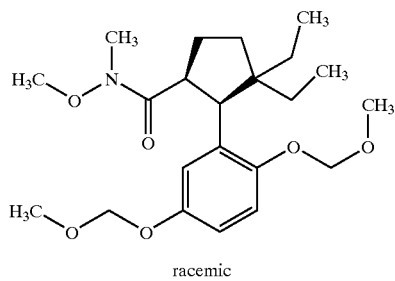

racemic

Cool a suspension of Preparation 22 (0.25 g, 0.77 mmol) and N,O-dimethylhydroxylamine hydrochloride (0.11 g, 1.16 mmol) in anhydrous THF (20 mL) to −10° C. in an ice/acetone bath, add isopropyl magnesium chloride (2.0M, 1.2 mL, 2.40 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.20 g, 74%) as a clear oil which is used without further characterization.

PREPARATION 30

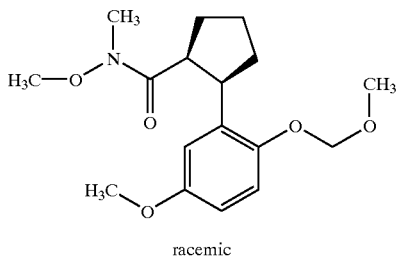

racemic

Cool a suspension of Preparation 23 (0.91 g, 3.07 mmol) and N,O-dimethylhydroxylamine hydrochloride (0.45 g, 4.64 mmol) in anhydrous THF (20 mL) to −10° C. in an ice/acetone bath, add isopropyl magnesium chloride (2.0M, 3.1 mL, 6.20 mmol), and stir the reaction for 30 minutes. Quench the reaction with saturated ammonium chloride. Add ethyl acetate and wash the organic layer washed with brine. Dry the organic layer over sodium sulfate, concentrate in vacuo, and flash chromatograph with 50% ethyl acetate/hexane to yield the title compound (0.36 g, 36%) as a clear oil which is used without further characterization.

PREPARATION 31

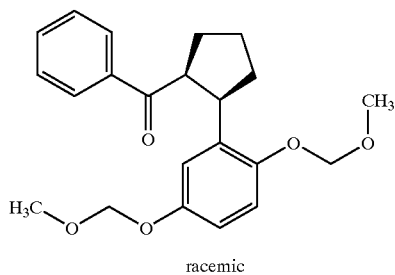

racemic

Add phenyl lithium (1.0 M in cyclohexane, 1.3 mL, 1.34 mmol) into a solution of Preparation 24 (0.43 g, 1.22 mmol) in anhydrous THF 30 mL) at 0° C. and stir the resulting solution for 30 minutes at 0° C. Quench the reaction with saturated sodium bicarbonate. Add ethyl acetate and wash with brine. Dry the organic layer over sodium sulfate, concentrate in vacuo, and flash chromatograph with 60% ethyl acetate/hexane to yield the title compound (0.28 g, 85%) as a clear oil. $^1$H NMR (CDCl$_3$): 7.61 (d, J=7.4, 2H), 7.37–7.33 (m, 1H), 7.24–7.19 (m, 2H), 6.77 (d, J=2.7, 1H), 6.66 (d, J=9.0, 1H), 6.60 (dd, J=3.1, 9., 1H), 5.00 (dd, J=6.6, 17.8, 2H), 4.84 (s, 2H), 4.32–4.29 (m, 1H), 3.84–379 (m, 1H), 3.42 (s, 3H), 3.38 (s, 3H), 2.32–1.95 (m, 5H), 1.80–1.72 (m, 1H).

PREPARATION 32

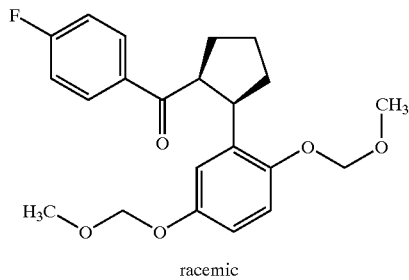

racemic

To 0.31 mL (2.8 mmol) of p-bromofluorobenzene in 10 mL of THF at −78° C. was added 3.4 mL (5.6 mmol) of 1.7 M tert-butyllithium. The mixture was cannulated into 0.7 g (2.0 mmol) of Preparation 24 in 10 mL of anhydrous THF at −78° C. with magnetic stirring, and all was allowed to come to room temperature. After 5 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes to give the title compound (0.41 g, 53%). $^1$H NMR (CDCl$_3$): 7.62 (m, 2H), 6.86 (m, 2H), 6.66 (m, 2H), 6.58 (m, 1H), 4.98 (dd, J=8.0, 17.0, 2H), 4.91 (s, 2H), 4.25 (m, 1H), 3.80 (m, 1H), 3.41 (s, 3H), 3.40 (s, 3H), 2.28–1.90 (m, 5H), 1.75 (m, 1H).

PREPARATION 33

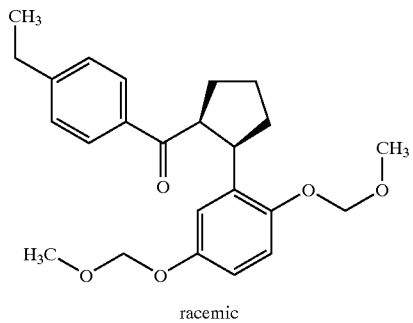

racemic

To 0.33 mL (2.4 mmol) of 4-bromo-ethylbenezene in 10 mL of THF at −78° C. was added 3.0 mL (5.0 mmol) of 1.7 M tert-butyllithium. The mixture was cannulated into 0.7 g (2.0 mmol) of Preparation 24 in 10 mL of anhydrous THF at −78° C. with magnetic stirring, and all was allowed to come to room temperature. After 5 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes/0.4% triethylamine to give the title compound (0.46 g, 58%). $^1$H NMR (CDCl$_3$): 7.54 (d, J=8.4, 2H), 7.03 (d, J=8.4, 2H), 6.76 (d, J=2.4, 1H), 6.67 (d, J=8.0, 1H), 6.58 (dd, J=8.0, 2.4, 1H), 5.00 (d, J=7.5, 1H), 4.96 (d, J=7.5, 1H), 4.85 (s, 2H), 4.26 (m, 1H), 3.80 (m, 1H), 3.40 (s, 3H), 3.38 (s, 3H), 2.58 (q, J=7.2, 2H), 2.26–1.92 (m, 5H), 1.65 (m, 1H), 1.17 (t, J=7.2, 3H).

PREPARATION 34

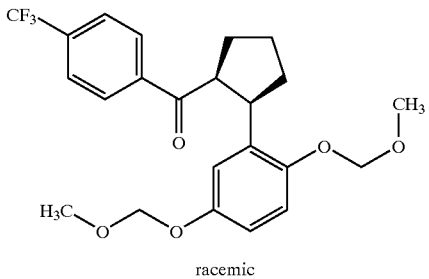

racemic

To 0.26 mL (1.8 mmol) of 4-bromo-α,α,α-trifluorotoluene in 10 mL of THF at −78° C. was added 2.15 mL (3.66 mmol) of 1.7 M tert-butyllithium. The mixture was cannulated into 0.59 g (1.67 mmol) of Preparation 24 in 10 mL of anhydrous THF at −78° C. with magnetic stirring, and all was allowed to come to room temperature. After 18 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes/0.4% triethylamine to give the title compound (0.24 g, 33%). $^1$H NMR (CDCl$_3$): 7.65 (d, J=8.8, 2H), 7.45 (d, J=8.8, 2H), 6.70 (s, 1H), 6.60 (m, 2H), 5.00 (d, J=7.5, 1H), 4.96 (d, J=7.5, 1H), 4.87 (s, 2H), 4.28 (m, 1H), 3.82 (m, 1H), 3.41 (s, 3H), 3.38 (s, 3H), 2.28 (m, 1H), 2.16–1.92 (m, 4H), 1.75 (m, 1H).

PREPARATION 35

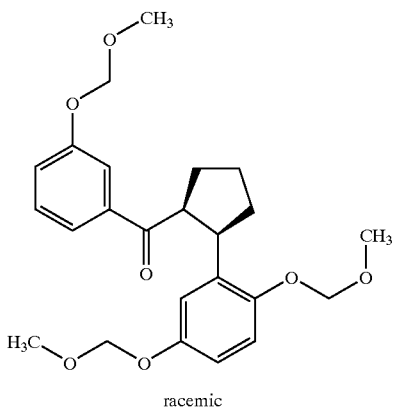

racemic

To 0.63 g (2.8 mmol) of 3-bromo-O-methoxymethylphenol 10 mL of THF at −78° C. was added 3.6 mL (6.1 mmol) of 1.7 M tert-butyllithium. The mixture was cannulated into 0.98 g (2.77 mmol) of Preparation 24 in 10 mL of anhydrous THF at −78° C. with magnetic stirring, and all was allowed to come to room temperature. After 18 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes/0.1% triethylamine to give the title compound (0.68 g, 57%). $^1$H NMR (CDCl$_3$): 7.27 (d, J=7.8, 1H), 7.20 (d, J=1.6, 1H), 7.13 (m, 1H), 7.02 (dd, J=7.8, 1.6, 1H), 6.75 (d, J=3.2, 1H), 6.68 (d, J=7.8, 1H), 6.60 (dd, J=7.8, 3.2, 1H), 5.09 (s, 2H), 5.01 (d, J=6.4, 1H), 4.97 (d, J=6.6, 1H), 4.87 (s, 2H), 4.25 (m, 1H), 3.78 (m, 1H), 3.47 (m, 1H), 3.43 (s, 3H), 3.41 (s, 3H), 3.38 (s, 3H), 2.25–1.92 (m, 4H), 1.72 (m, 1H).

PREPARATION 36

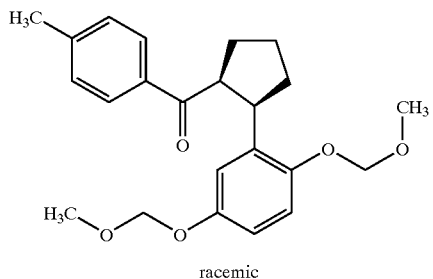

racemic

To 0.31 mL (3.0 mmol) of 4-bromotoluene in 10 mL of THF at −78° C. was added 3.6 mL (6.1 mmol) of 1.7 M tert-butyllithium. The mixture was cannulated into 0.98 g (2.77 mmol) of Preparation 24 in 10 mL of anhydrous THF at −78° C. with magnetic stirring, and all was allowed to come to room temperature. After 5 hours, the mixture was partitioned between diethylether and saturated sodium bicarbonate aqueous. The organic layer was washed with water, saturated brine, dried over anhydrous sodium sulfate, concentrated in vacuo, and flash chromatographed on silica gel with 10% ethylacetate/hexanes to give the title compound (0.38 g, 36%). $^1$H NMR (CDCl$_3$): 7.52 (d, J=7.6, 2H), 7.01 (d, J=8.0, 2H), 6.76 (d, J=3.0, 1H), 6.69 (d, J=8.8, 1H), 6.60 (dd, J=8.8, 3.0, 1H), 5.01 (d, J=6.8, 1H), 4.96 (d, J=6.6, 1H), 4.86 (s, 2H), 4.24 (m, 1H), 3.79 (m, 1H), 3.47 (m, 1H), 3.40 (s, 3H), 3.38 (s, 3H), 2.29 (s, 3H), 2.28–1.92 (m, 4H), 1.74(m, 1H).

EXAMPLE 1

Preparation of (±)-2-Phenyl-6-hydroxy-cyclopentyl [c]3,4-dihydro-2H-1-benzopyran

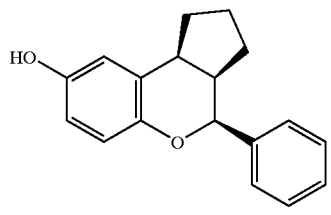

racemic

Heat a solution of Preparation 31 (0.14 g, 0.38 mmol), triethylsilane (2 mL), and TFA (1 mL) in dichloromethane (5 mL) to 60° C. for 18 hours. Cool to ambient temperature and quench with saturated sodium bicarbonate. Add ethyl acetate, wash with brine, dry organic layer, and concentrate in vacuo. Chromatograph with 95% dichloromethane/hexane to yield the title compound (0.10 g, 98%) as an off white solid. $^1$H NMR (CDCl$_3$): 7.47 (d, J=2.4, 2H), 7.40–7.36 9m, 2H), 7.30–7.27 (m, 1H), 6.80 (d, J=8.6, 1H), 6.67 (d, J=3.1, 1H), 6.60 (dd, J=3.1, 8.6, 1H), 5.11 (d, J=1.0, 1H), 4.70 (s, 1H), 3.47–3.45 (m, 1H), 2.64–2.57 (m, 1H), 2.16–2.10 (m, 1H), 1.83–1.76 (m, 1H), 1.70–1.13 (m, 4H). MS calcd. 266.1; MS (M−1) 265.2.

EXAMPLE 2

Preparation of (±)-2-(4-Fluorophenyl)-6-hydroxy-cyclopentyl[c]3,4-dihydro-2H-1-benzopyran

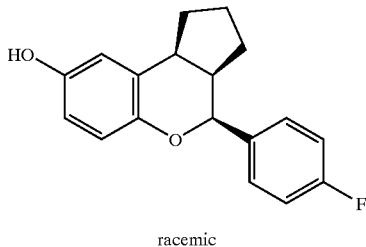

racemic

Heat a solution of Preparation 32 (0.41 g, 1.05 mmol), triethylsilane (0.75 mL), and TFA (0.75 mL) in 1,2-dichloroethane (20 mL) to 60° C. for 18 hours. Cool to ambient temperature and quench with saturated potassium sodium tartrate aqueous. Add diethyl ether, wash with brine, dry organic layer, and concentrate in vacuo. Chromatograph on silica gel with 10% ethylacetate/0.4% triethylamine/hexane. The product containing band was evaporated and the residue slurried in hexanes with a little diethylether. The solids were filtered under vacuum and air dried to yield the title compound (0.072 g, 24%) as a solid. $^1$H NMR (DMSO-d6): 8.88 (s, 1H), 7.48 (dd, J=8.8, 6.0, 2H), 7.20 (dd, J=8.8, 8.8, 2H), 6.67 (d, J=8.6, 1H), 6.57 (d, J=2.8, 1H), 6.49 (dd, J=2.8, 8.6, 1H), 5.06 (s, 1H), 3.40 (m, 1H), 2.60 (m, 1H), 2.08 (m, 1H), 1.65 (m, 1H), 1.40 (m, 3H), 1.22 (m, 1H). MS calcd. 284.3; MS (M−1) 283.1.

EXAMPLE 3

Preparation of (±)-2-(4-ethylphenyl)-6-hydroxy-cyclopentyl[c]3,4-dihydro-2H-1-benzopyran

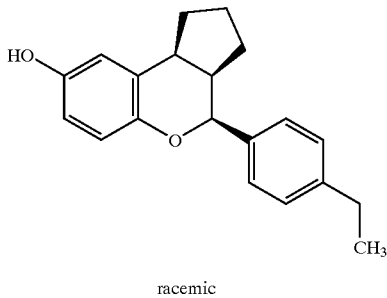

racemic

To a solution of Preparation 33 (0.46 g, 1.10 mmol) in anhydrous methanol (15 mL) under nitrogen gas bubbling to purge of oxygen was added p-toluenesulfonic acid (0.17 g, 0.86 mmol). The bubbler was removed, and the resulting solution was heated to 50° C. for 18 hours under a nitrogen atmosphere. To the mixture at ambient temperature was added bromocreosol green (~1 mg) and sodium cyanoborohydride (0.35 g, 5.50 mmol). Methanol saturated with HCl (gas) was added portionwise over time to maintain the yellow color. After no more spontaneous color change to blue was observed, the mixture was partitioned between diethylether and saturated potassium sodium tartrate aqueous. The organic layer was dried over anhydrous sodium sulfate, concentrated in vacuo, and flash chromatographed on silica gel with 3% diethylether/methylene chloride to give 0.17 g (52%) of the title compound. $^1$H NMR (DMSO-d6): 8.85 (s, 1H), 7.35 (d, J=8.0, 2H), 7.19 (d, J=8.0, 2H), 6.78 (d, J=8.4, 1H), 6.65 (d, J=2.4, 1H), 6.48 (dd, J=2.4, 8.4, 1H), 5.02 (s, 1H), 3.44 (m, 1H), 2.60 (q, J=7.2, 2H), 2.46 (m, 1H), 2.08 (m, 1H), 1.66 (m, 1H), 1.48–1.11 (m, 4H), 1.21 (t, J=7.2, 3H). MS calcd. 294.4; MS (M−1) 293.2 (M+1) 295.1.

EXAMPLE 4

Preparation of (±)-2-(4-Trifluoromethylphenyl)-6-hydroxy-cyclopentyl[c]3,4-dihydro-2H-1-benzopyran

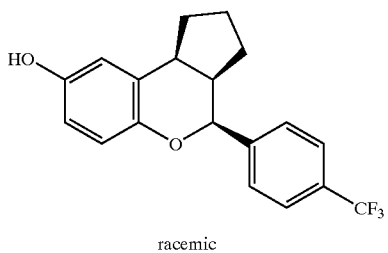

racemic

Heat a solution of Preparation 34 (0.14 g, 0.38 mmol), triethylsilane (0.5 mL), and TFA (0.5 mL) in 1,2-dichloroethane (20 mL) to 60° C. for 5 hours. Cool to ambient temperature and quench with saturated potassium sodium tartrate aqueous. Add diethyl ether, wash with brine, dry organic layer, and concentrate in vacuo. Chromatograph on silica gel with 5% ethylacetate/hexane. The product containing band was evaporated and the residue slurried in hexanes. The solids were filtered under vacuum and air dried to yield the title compound (0.070 g, 55%) as a solid. $^1$H NMR (CDCl$_3$): 7.62 (d, J=8.4, 2H), 7.56 (d, J=8.4, 2H), 6.79 (d, J=8.8, 1H), 6.66 (d, J=2.7, 1H), 6.59 (dd, J=2.7, 8.8, 1H), 5.13 (s, 1H), 4.43 (s, 1H), 3.48 (m, 1H), 2.61 (m, 1H), 2.13 (m, 1H), 1.78 (m, 1H), 1.723–1.62 (m, 3H), 1.28 (m, 1H). MS calcd. 334.3; MS (M−1) 333.0.

EXAMPLE 5

Preparation of (±)-2-(3-Hydroxyphenyl)-6-hydroxy-cyclopentyl[c]3,4-dihydro-2H-1-benzopyran

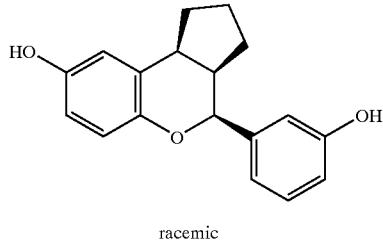

racemic

To a solution of Preparation 35 (0.34 g, 0.79 mmol) in anhydrous methanol (15 mL) under nitrogen gas bubbling to purge of oxygen was added p-toluenesulfonic acid (0.112 g, 0.59 mmol). The bubbler was removed, and the resulting solution was heated to 50° C. for 18 hours under a nitrogen atmosphere. To the mixture at ambient temperature was added bromocreosol green (~1 mg) and sodium cyanoborohydride (0.25 g, 4.0 mmol). Methanol saturated with HCl (gas) was added portionwise over time to maintain the yellow color. After no more spontaneous color change to blue was observed, the mixture was partitioned between ethylacetate sodium bicarbonate aqueous. The organic layer was dried over anhydrous sodium sulfate, concentrated in vacuo, and flash chromatographed on silica gel with 5% diethylether/methylene chloride to give 0.14 g (63%) of the title compound. $^1$H NMR (CDCl$_3$): 7.14 (t, J=8.6, 1H), 6.88 (s, 1H), 6.83 (d, J=8.6, 1H), 6.65 (d, J=8.8, 2H), 6.55 (d, J=2.8, 1H), 6.47 (dd, J=8.8, 2.8, 1H), 4.45 (s, 1H), 3.42 (m, 1H), 2.58 (m, 1H), 2.06 (m, 1H), 1.64 (m, 1H), 1.48–1.16 (m, 4H). MS calcd. 282.3; MS (M−1) 281.2. Fore and aft bands from normal phase chromatography were isolated and chromatographed on a C18 reverse phase column with acetonitrile/water (50:50) to give another 56 mg (78% total yield) after lyophilization of 541525.

EXAMPLE 6

Preparation of (±)-2-(4-Methylphenyl)-6-hydroxy-cyclopentyl[c]3,4-dihydro-2H-1-benzopyran

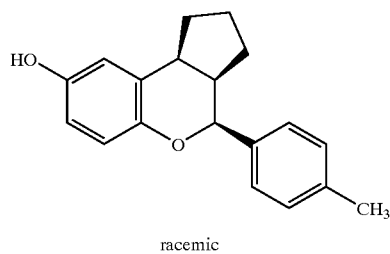

racemic

To a solution of Preparation 36 (0.38 g, 0.99 mmol) in anhydrous methanol (15 mL) under nitrogen gas bubbling to purge of oxygen was added p-toluenesulfonic acid (0.14 g, 0.73 mmol). The bubbler was removed, and the resulting solution was heated to 50° C. for 18 hours under a nitrogen atmosphere. To the mixture at ambient temperature was added bromocreosol green (~1 mg) and sodium cyanoborohydride (0.31 g, 5.0 mmol). Methanol saturated with HCl (gas) was added portionwise over time to maintain the yellow color. After no more spontaneous color change to blue was observed, the mixture was partitioned between ethylether and water. The organic layer was dried over anhydrous sodium sulfate, concentrated in vacuo, and flash chromatographed on silica gel with 5% ethylacetate/hexanes to give 0.20 g (72%) of the title compound. $^1$H NMR (CDCl3): 7.33 (d, J=7.2, 2H), 7.17 (d, J=7.2, 2H), 6.78 (d, J=8.8, 1H), 6.64 (s, 1H), 6.58 (d, J=8.4, 1H), 5.06 (s, 1H), 4.40 (s, 1H), 3.45 (m, 1H), 2.58 (m, 1H), 2.35 (s, 3H), 2.12 (m, 1H), 1.78 (m, 1H), 1.62 (m, 1H), 1.57–1.22 (m, 3H). Microanalysis calcd for C19H20-02: C, 81.40, H, 7.19; found C, 81.18, H 7.25.

TEST PROCEDURES
ER Binding Assay

The competition ER binding assay was run in a buffer containing 50 mM N-[2-hydroxyethyl]piperazine-N'-[2-ethanesulfonic acid (Hepes) pH 7.5, 1.5 mM EDTA, 150 mM NaCl, 10% glycerol, 1 mg/mL ovalbumin, 5 mM DTT, 0.025 μCi per well of $^3$H-Estradiol(NEN #NET517 at 118 Ci/mmol, 1 mCi/mL), and 10 ng/well ERAlpha or ERbeta Receptor (PanVera). Competing compounds were added at 10 different concentrations. Non-specific binding was determined in the presence of 1 μM of E2 (17-β Estradiol, Sigma, St. Louis, Mo.). The binding reaction (140 μL) was incubated for 4 hours at room temperature, then 70 μL of cold dextran coated charcoal (DCC) buffer was added to each reaction (DCC buffer was prepared by adding 0.75 g of charcoal[Sigma] and 0.25 g of dextran [Pharmacia] per 50 mL of assay buffer). The incubation plates were mixed for 8 minutes on an orbital shaker at 4° C. and then centrifuged at 3,000 rpm for 10 minutes at 4° C. An aliquot of 120 μl of the mix was transferred to another 96-well, white flat bottom plate (Costar) and 175 μl of Wallac Optiphase Hisafe 3 scintillation fluid was added to each well. The plates were sealed and then shaken vigorously on an orbital shaker. After an incubation of 2.5 hrs, the radioactivity was counted in a Wallac Microbeta counter. The IC$_{50}$ and percent inhibition at 10 μM were calculated. The K$_d$ for $^3$H-Estradiol was determined by saturation binding to ERα and ERβ receptors. The IC$_{50}$ values for compounds were converted to K$_i$ values using the Cheng-Prusoff equation and the K$_d$ values were determined by saturation binding assay. Compounds of Examples 1–6 are active in the assay as described. The compounds of Examples 1–6 bind to the ER beta receptor with a K$_i$ of less than 100 nM. Preferred compounds bind to the ER beta receptor with a K$_i$ of less than 50 nM. More preferred compounds bind to the ER beta receptor with a K$_i$ of less than 20 nM. Compounds that are selective to binding to the ER beta receptor compared to the ER alpha receptor bind to the ER beta receptor with a lower K$_i$ compared to the K$_i$ for the ER alpha receptor. Preferred selective ER beta compounds bind to ER beta receptor with a K$_i$(ER alpha)/K$_i$(ER beta) ratio of greater than 4 as shown in Table 1.

TABLE 1

Ratio of K$_i$(nM)ER alpha/K$_i$(nM) ER beta

| Example | K$_i$(nM)ER alpha/K$_i$(nM) ER beta |
|---|---|
| 1 | 5.5 |
| 2 | 5.0 |
| 3 | 2.6 |
| 4 | 6.9 |
| 5 | 3.5 |
| 6 | 12.6 |

LNCaP Human PCa Xenograft Assay

ERbeta agonist are evaluated for their effects on the growth of androgen-sensitive LNCaP human prostatic cancer (PCa) xenografts grown in intact sexually mature (5–6 weeks old) Hsd: Athymic Nude-nu (Athymic Nude) male mice. 2.0×10$^6$ LNCaP tumor cells are injected bilaterally by the subcutaneous route into the pre-tracheal region of testicular intact male mice. Mice are castrated via the scrotal route to serve as the positive control group. Test compounds are administered once per day by subcutaneous or gavage administration at multiple dose levels in a volume of 0.2 ml to xenograft-bearing mice starting on the day following tumor injection. Test compounds are reformulated weekly based on average group mean body weights. The vehicle for these studies is 1% carboxymethyl cellulose (CMC) with 0.25% Tween 80. Body weights and tumor measurements are recorded on a weekly basis and entered directly into a JMP™ (SAS; Cary, N.C.) spreadsheet from electronic caliper measurement. Tumor volumes in mm$^3$ are calculated in JMP using the following formula: L×W×H×0.5236. Tumor and body weight responses for individual mice are recorded on a weekly basis. When LNCaP tumor volumes enter log-phase expansion, lesions are measured every 3–4 days. Growth rates are determined using linear modeling of the log tumor values and time to treatment failure (tumor vol=1300–1500 mm$^3$) are determined using a linear extrapolation model (SAS; Cary, N.C.). Because of humane animal use considerations, animals are sacrificed when their tumor volumes approach 1200–1400 mm$^3$. At necropsy, final tumor measurement and body weights are recorded and whole blood is obtained via cardiac puncture and allowed to clot on ice. Serum is transferred to appropriately labeled 0.5 ml Eppendorf micro tubes, and samples are stored at –80° C. for biomarker analysis.

General Rat Preparation Procedure

Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with a compound of formula (I) ("F-I") is initiated. 17α-ethynyl estradiol or F-I is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH 8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosinophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from these animals are also scanned by quantitative computed tomography. In accordance with the above procedures, F-I or ethynyl estradiol ($EE_2$) in 20% hydroxypropyl β-cyclodextrin are orally administered to test animals.

Therapeutic Methods of Use and Dosages

Various diseases and conditions described to be treated herein, are well known and appreciated by those skilled in the art. It is also recognized that one skilled in the art may affect the associated diseases and conditions by treating a patient presently afflicted with the diseases or conditions or by prophylactically treating a patient afflicted with the diseases or conditions with a therapeutically effective amount of the compounds of formula (I).

As used herein, the term "patient" refers to a warm blooded animal such as a mammal that is afflicted with a particular inflammatory disease state. It is understood that guinea pigs, dogs, cats, rats, mice, horses, cattle, sheep, and humans are examples of animals within the scope of the meaning of the term.

As used herein, the term "therapeutically effective amount" of a compound of formula (I) refers to an amount which is effective in controlling diseases and conditions associated with estrogen receptor-beta mediated diseases such as prostate cancer, benign prostatic hyperplasia, testicular cancer, cardiovascular diseases, neurodegenerative disorders, urinary incontinence, CNS conditions, GI tract conditions, and osteoporosis. The term "controlling" is intended to refer to all processes wherein there may be a slowing, interrupting, arresting, or stopping of the progression of the diseases and conditions described herein, but does not necessarily indicate a total elimination of all disease and condition symptoms, but does include prophylactic treatment of the diseases and conditions associated with estrogen receptor-beta mediated diseases such as prostate cancer, benign prostatic hyperplasia, testicular cancer, cardiovascular diseases, neurodegenerative disorders, urinary incontinence, CNS, GI tract conditions, and osteoporosis.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (I) is expected to vary from about 0.001 milligram per kilogram of body weight per day (mg/kg/day) to about 100 mg/kg/day. Preferred amounts can be determined by one skilled in the art.

In effecting treatment of a patient afflicted with the diseases and conditions described above, a compound of formula (I) can be administered in any form or mode which makes the compound bioavailable in a therapcutically effective amount, including oral, inhalation, and parenteral routes. For example, compounds of formula (I) can be administered orally, by inhalation of an aerosol or dry powder, subcutaneously, intramuscularly, intravenously, transderrnally, intranasally, rectally, topically, and the like. Oral or inhalation administration is generally preferred for treatment of respiratory diseases, e.g. asthma. One skilled in the art of preparing formulations can readily select the proper form and mode of administration depending upon the particular characteristics of the compound selected, the disease or condition state to be treated, the stage of the disease or condition, and other relevant circumstances. (Remington's Pharmaceutical Sciences, 18th Edition, Mack Publishing Co. (1990)).

The compounds of the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility and the like.

In another embodiment, the present invention provides pharmaceutical compositions comprising a therapeutically effective amount of a compound of formula (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (I) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system that dispenses the compounds of the present invention or a formulation thereof. Formulations for administration by inhalation of compounds of formula (I) may be delivered in single phase, bi-phasic, or tri-phasic systems. A variety of systems are available for the administration by aerosols of the compounds of formula (I). Dry powder formulations are prepared by either pelletizing or milling the compound of formula (I) to a suitable particle size or by admixing the pelletized or milled compound of formula (I) with a suitable carrier material, such as lactose and the like. Delivery by inhalation includes the necessary container, activators, valves, subcontainers, and the like. Preferred aerosols and dry powder formulations for administration by inhalation are able to be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (I) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

We claim:
1. A compound of according to the formula:

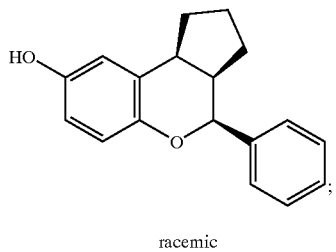

racemic or a pharmaceutically acceptable salt or enantiomer thereof.
2. A compound according to the formula:

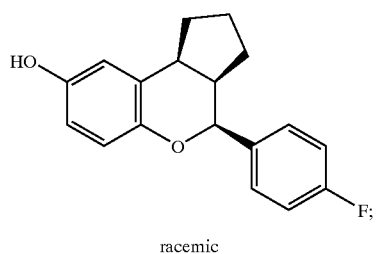

racemic or a pharmaceutically acceptable salt or enantiomer thereof.
3. A compound according to the formula:

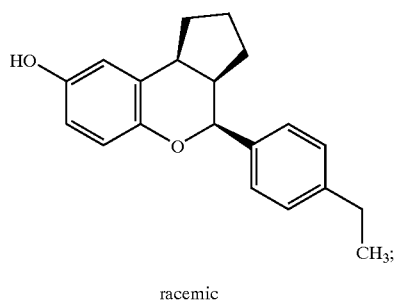

racemic or a pharmaceutically acceptable salt or enantiomer thereof.
4. A compound according to the formula:

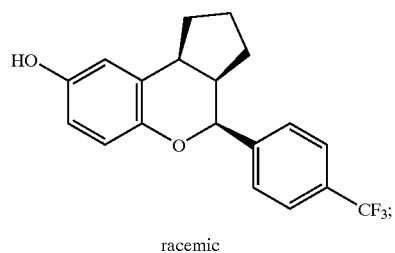

racemic or a pharmaceutically acceptable salt or enantiomer thereof.

5. A compound according to the formula:

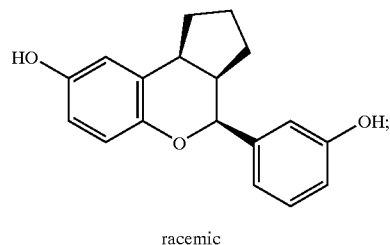

racemic or a pharmaceutically acceptable salt or enantiomer thereof.
6. A compound according to the formula:

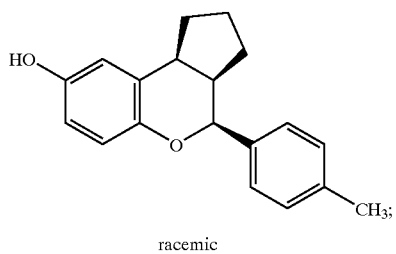

racemic or a pharmaceutically acceptable salt or enantiomer thereof.
7. A compound selected from the group consisting of:
a) (±)-2-phenyl-6-hydroxy-cyclopentyl[c]3,4-dihydro-2H-1-benzopyran,
b) (±)-2-(4-fluorophenyl)-6-hydroxy-cyclopentyl[c]3,4-dihydro-2H-1-benzopyran,
c) (±)-2-(4-ethylphenyl)-6-hydroxy-cyclopentyl[c]3,4-dihydro-2H-1-benzopyran,
d) (±)-2-(4-trifluoromethylphenyl)-6-hydroxy-cyclopentyl[c]3,4-dihydro-2H-1-benzopyran,
e) (±)-2-(3-hydroxyphenyl)-6-hydroxy-cyclopentyl[c]3,4-dihydro-2H-1-benzopyran,
f) (±)-2-(4-methylphenyl)-6-hydroxy-cyclopentyl[c]3,4-dihydro-2H-1-benzopyran.
8. A pharmaceutical composition comprising a compound according to claim 7 and a pharmaceutically acceptable carrier.
9. A method of selectively binding to estrogen receptor beta in a patient in need thereof comprising administering to said patient a therapeutically effective amount of a compound according to claim 7.
10. A method of treating a patient afflicted with an estrogen receptor beta mediated disease condition comprising administering to said patient a therapeutically effective amount of a compound according to claim 7.
11. A method of treating prostate cancer in a patient in need thereof comprising administering to said patient a therapeutically effective amount of a compound according to claim 7.
12. A method according to claim 10 wherein said patient is a human.
13. A method according to claim 11 wherein said patient is a human.

* * * * *